(12) United States Patent
Severson et al.

(10) Patent No.: US 9,265,527 B1
(45) Date of Patent: Feb. 23, 2016

(54) BIRTH EASE METHOD AND DEVICE

(76) Inventors: Gregory C. Severson, Eau Claire, WI (US); Tony Curtis, Eau Claire, WI (US)

( * ) Notice: Subject to any disclaimer, the term of this patent is extended or adjusted under 35 U.S.C. 154(b) by 189 days.

(21) Appl. No.: 13/476,675

(22) Filed: May 21, 2012

(51) Int. Cl.
*A61B 17/42* (2006.01)
(52) U.S. Cl.
CPC ............. *A61B 17/42* (2013.01); *A61B 17/4241* (2013.01)
(58) Field of Classification Search
CPC ............... A61B 17/42; A61B 17/4241; A61H 2205/08; A61H 2205/083; A61H 2201/5056; A61H 2201/0103
USPC .................................... 606/119–125; 434/273
See application file for complete search history.

(56) References Cited

U.S. PATENT DOCUMENTS

| | | | |
|---|---|---|---|
| 2,597,637 A | 5/1952 | Heidenwolf | |
| 4,403,801 A * | 9/1983 | Huff et al. ................. | 294/119.3 |
| 4,576,154 A | 3/1986 | Hyman et al. | |
| 4,836,194 A | 6/1989 | Sebastian et al. | |
| 5,174,281 A | 12/1992 | Lee | |
| 5,405,356 A | 4/1995 | Hahn et al. | |
| 5,643,563 A | 7/1997 | Hahn et al. | |
| 5,817,499 A | 2/1999 | Hahn et al. | |
| 5,928,175 A | 7/1999 | Tanaka | |
| 2005/0242639 A1 | 11/2005 | Ha | |
| 2007/0172804 A1 | 7/2007 | Allen et al. | |
| 2011/0196269 A1 * | 8/2011 | Arkans ........................... | 601/15 |

* cited by examiner

*Primary Examiner* — Julian W Woo
*Assistant Examiner* — Michael Mendoza
(74) *Attorney, Agent, or Firm* — Tipton L. Randall

(57) ABSTRACT

A method for easing child birth and, more particularly, to a device for practicing the method for easing child birth and, most particularly, to a device for easing child birth controlled by the individual giving birth to the child. The device mechanically replaces a "manual" contact, which can be applied to the pelvis of a woman in labor, for the purpose of aiding the expulsion of the baby, and reduce the pain and discomfort associated with this process. The device mechanically compresses the ilium portion of the pelvis medially and posteriorly, simultaneously. The pressure applied by the device is under full control of the patient, so that pressure is applied slowly and progressively to a point of maximum comfort. The pressure is decreased immediately upon demand by the patient. The duration of the application of compression corresponds with the length of the contraction period for the woman.

10 Claims, 7 Drawing Sheets

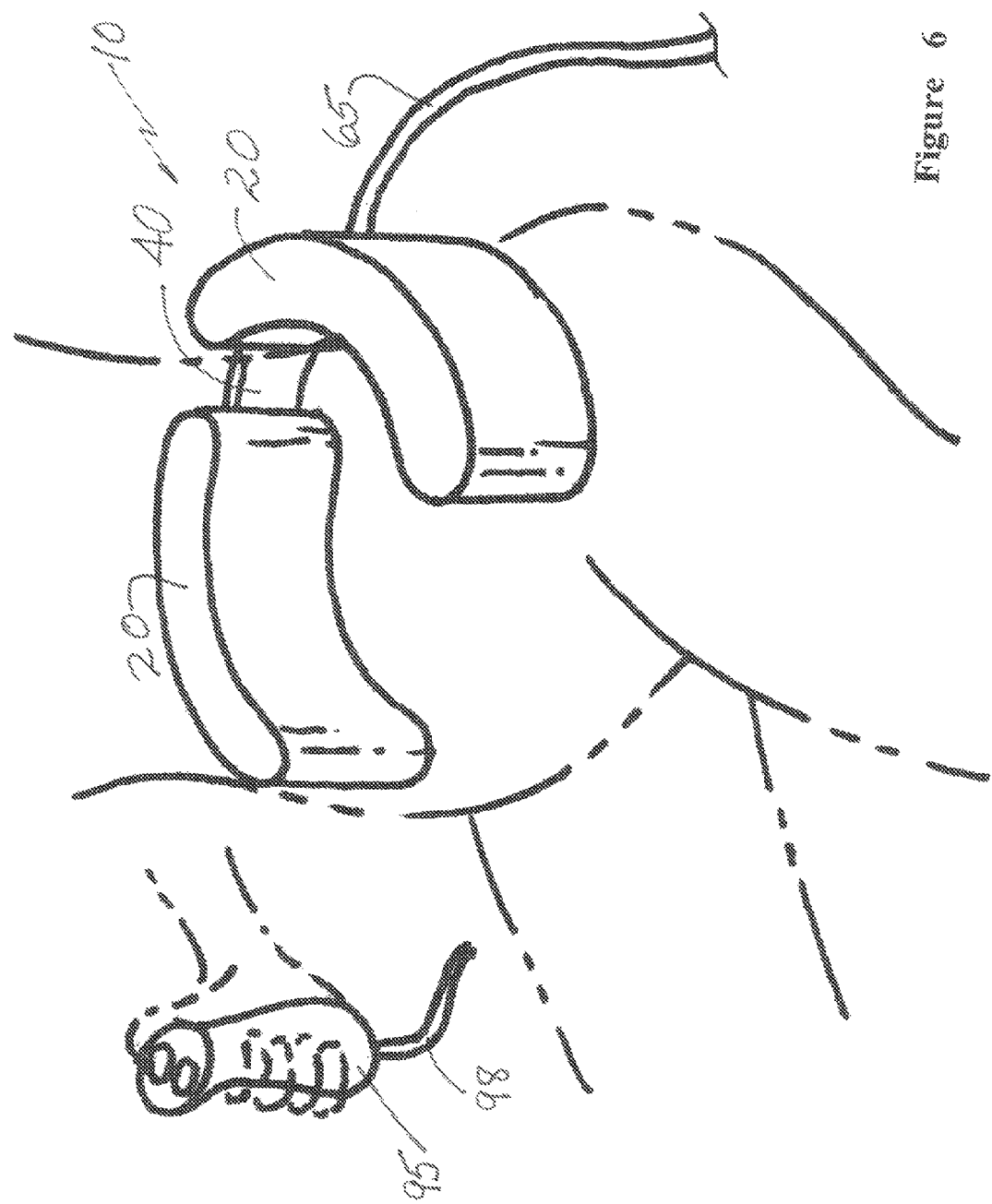

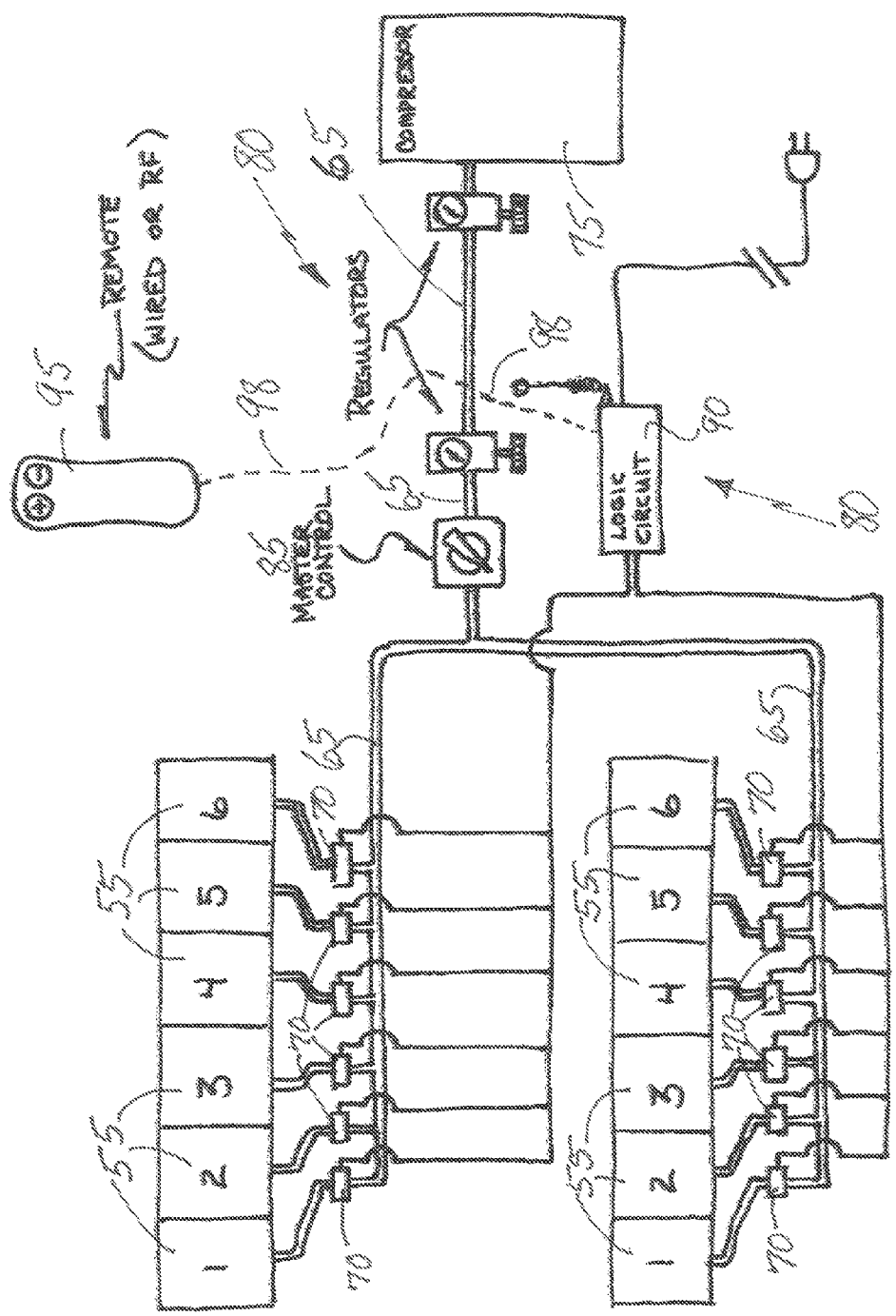

BIRTH EASE METHOD AND DEVICE

CROSS-REFERENCE TO RELATED APPLICATIONS, IF ANY

Not applicable.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates to a method for easing child birth and, more particularly, to a device for practicing the method for easing child birth and, most particularly, to a device for easing child birth, which is controlled by the individual giving birth to the child.

2. Background Information

Child birth is often a traumatic physical and emotional process that involves passage of the child through the birth canal of the mother. The process is nearly always painful and can put the well being of both the mother and child in jeopardy. Various medications can be used to ease the pain of the mother during the process, but such medications are not without risk to both the mother and child. Various mechanical devices have been developed to assist the child birth process. Several inventions concerned with devices that are applied to the exterior of the mother to assist in child birth have been granted patents.

Heidenwolf, in U.S. Pat. No. 2,597,637, describes an obstetrical apparatus that includes a belt with an inflatable bladder that is secured around the abdomen of a parturient woman. The belt is positioned such that inflation of the bladder applies pressure toward the belly between the hips and bottom of the uterus of the woman. The belt is held in place by a strap that is secured to the upper thigh of the woman.

In U.S. Pat. No. 4,576,154, Hyman et al. disclose an orthopedic belt that eases sacroiliac joint pain by compressing soft pelvic tissue against the sacrum and ilium, to support and immobilize the sacroiliac joints. The belt consists solely of flat, woven webbing forming a band about four to six inches wide, and a fastening device at the front. The belt encircles the patient at the level between the anterior superior iliac spines and the greater trochanters of the femurs. It is fastened with enough tension to compress the soft tissue, as desired. Ends of the band forming the belt are fastened together at an angle, which is selected to pass the belt horizontally across the back and to accommodate the shape of the patient's hips. The ends of the band are cut off in a taper so that no square corners are exposed. Various fastening means to place and maintain tension on the band may be used, including flexible straps extending from one end of the band through loops on the other and back to the first end, where they are connected together with cooperating press-holding pads such as Velcro™ hook and eye material.

Sebastian et al., in U.S. Pat. No. 4,836,194, describe a therapeutic appliance for application to the lumbar spine. The appliance follows the contours of the iliac crests and overlies the sacrum and sacroiliac joints, as well as anchors below the posterior superior iliac spines of the human body. The appliance includes an external shell having a length sufficient to extend around the abdominal region of the body with fasteners at opposite ends of the shell and an air bladder disposed on the shell. The air bladder has a plurality of air chambers, including elongated air chambers which extend transversely to the longitudinal direction of the shell with lower ends thereof shaped to lie above the iliac crests. The device includes a lower longitudinally extending air chamber and an anchoring air chamber between the longitudinally extending air chamber and the outer edge of the bladder. The anchoring air chamber extends arcuately from a central portion of the air bladder toward the opposite ends of the shell and is positioned to lie below the posterior superior iliac spines to prevent upward riding of the therapeutic appliance when in place on the human body and to provide support for the sacroiliac joints. The appliance may also include belts on the outside thereof for tightening the air chambers against the wearer's lumbar spine and sacroiliac joints. Pockets can be provided on the inside of the appliance for applying hot or cold packs to the back muscles of the wearer of the appliance.

U.S. Pat. No. 5,174,281 by Lee discloses a pneumatic cuff assembly fitting over and around the entire maternal abdomen. The cuff is intermittently inflated to a low and safe pressure in synchrony with the mother's voluntary straining efforts in order to augment the intra-abdominal pressure to assist the delivery of the fetus at the final stage of child birth. Near the end of obstetric labor, the cuff is applied on the abdomen, parts are connected, and the reservoir tank pressurized to a recommended pressure of twenty pounds per square inch. At the final stage of delivery and synchronous with the mother's voluntary straining, the cuff is inflated. When the voluntary straining stops, the cuff is manually deflated quickly. The setting of the pressure reducer/regulator is to be determined by the physician or midwife. Two to four pounds per square inch seems appropriate. The amount of additional expelling force can be roughly estimated at two pounds per square inch of cuff pressure, which is considered low and safe, and at ten square inches of cross-sectional area of a fetal head, the force is twenty pounds, which is more than is safely applied with a pair of outlet forceps. Generally speaking, a pushing force is safer on the mother and the child then a pulling force.

In U.S. Pat. No. 5,405,356, Hahn et al. describe a childbirth-assisting device that uses an automatically synchronized, expandable pneumatic girdle to externally augment the secondary force of labor. The pneumatic girdle is fitted around the abdomen of the woman and the girdle is inflated to create a downward pressure on the abdomen when a contraction occurs. The synchronization of the girdle's inflation and the contractions is provided by an electronic controller, which receives a signal from an intra-uterine monitor indicating a contraction and causes the girdle to inflate at a certain rate until a preset intra-uterine pressure is attained. Once the intra-uterine pressure reaches the preset pressure, the girdle pressure is maintained until the offset of the contraction is detected, at which time the girdle is deflated.

Hahn et al., in U.S. Pat. Nos. 5,645,563 and 5,871,499, disclose a childbirth-assisting device that uses an automatically synchronized, expandable pneumatic girdle to externally augment the secondary force of labor. The girdle, through which the pressure is applied, is fitted around the abdomen of the woman. An inflatable bladder within the girdle is inflated to create a downward pressure on the abdomen upon detection of a contraction. External pressure monitors which detect contractions may be attached directly to the girdle, and the girdle is configured to assure that the bladder is correctly positioned at all times. The external pressure monitors include a solid state force sensor, embedded within a pliable housing, which is conformable to the patient's abdomen to improve accuracy. A member may be provided to prevent multiple uses of a girdle to assure the integrity of the girdle during use.

U.S. Pat. No. 5,928,175 by Tanaka discloses a medical corset that includes a hip band portion composed of an elastic material for covering both the sacroiliac region and the hip joint region and a pair of femoral region holding portions, coupled below the buttock portion of this hip band portion to be fixed on the thighs. When this corset is put on a body, the sacroiliac region and the hip joint region are compressed and protected by the hip band portion and, thus, a lame hip due to a trouble of these joints is lightened. When putting the medical corset on the body, the hip band portion is first wound around the hip region. The hip band portion, which is capable of entirely covering both the sacroiliac region and the hip joint region and is composed of an elastic material, keeps the hip region in a somewhat compressed condition. When the pair of femoral region holding means, coupled to the hip band portion, is fixed on the right and left thighs, the attachment of the medical corset is completed. In this condition, in which the femoral region holding means are fixed on the thighs and are coupled on the buttock side, the entire corset is prevented from shifting upward even if bending and stretching are repeated, for example. The buttock side is the region extending from the buttocks to the back.

Ha, in U.S. Patent Application Publication No. 2005/0242639, describes a pelvis remedial seat device and a control method thereof for remedying into its original place a woman's widened pelvis after child birth. The pelvis remedial seat device comprises a seat (10), a seat cushion (11) on which an occupant is seated and left/right seat sides (12a, 12b), provided uprightly at each side end of the seat cushion (11). A pair of air bags (20a, 20b) nested on an inner side of each side are expanded or contracted by air supplied into or discharged from the inside of the air bag. An air injection means for providing air pressure to the air bags (20a, 20b) is also present. The expanding air pressure in the air bags presses the pelvis portion of an occupant. Accordingly, the air pressure can artificially press the pelvis portion of the woman, when seated or lying down, without constraining the human body so that rapid recovery of the pelvis can be attained.

Applicants have devised a method for easing child birth and, more particularly, to a device for practicing the method for easing child birth and, most particularly, to a device for easing child birth, which is controlled by the individual giving birth to the child.

SUMMARY OF THE INVENTION

The invention is directed to a device to assist in the birth of a child. The birth ease device is designed to mechanically replace a "manual" contact, which can be applied to the pelvis of a woman in labor (delivering of a baby), for the purpose of aiding the expulsion of the baby, and also significantly reduce the pain and discomfort associated with this process. The birth ease device compresses the ilium portion of the pelvis medially and posteriorly, simultaneously. The pressure applied by the birth ease device is under full control of the patient, or a qualified technician, so that the pressure is applied slowly and progressively to a point of maximum comfort, but the pressure can be decreased immediately upon demand by the patient. Preferably, the duration of the application of compression corresponds with the length of the contraction period for the woman.

The birth ease device includes a pair of contact members that are contoured to fit the "ala" of the ilium and are adjustable to fit a range of sizes. The pair of opposed contact members each has an opposed concave surface therein forming a contact volume there between. Each opposed contact member includes a motive mechanism selectively actuated to vary the contact volume between the opposed contact members. A control mechanism is operatively connected to each opposed motive mechanism to selectively increase and decrease the contact volume between the opposed contact members. The motive mechanism is selectively controlled by the woman to increase and decrease the contact volume occupied by the woman's pelvis, thereby selectively applying and releasing pressure to the woman's pelvis, and assisting delivery of a child.

The birth ease device adds compressive pressure to the "ala" of the ilium. The medial pressure exerted by the birth ease device leverages the pelvis at the sacroiliac joints. This pressure is superior to a line drawn through the sacroiliac joints and causes reduced pressure inferior to this line, mainly affecting the symphysis pubis and the obturator foramen. The pressure applied by the concave, contact members eases the pressure exerted by the emerging head of the baby at the "obturator foramen." The applied pressure significantly decreases the pain associated with the birth process and aids the efficiency of the baby's head in forcing the obturator to enlarge.

For safety purposes, the pressure applied by the birth ease device is applied slowly, while reduction of the pressure can be immediate and absolute. However, a slow reduction of pressure comparable to the rate of application is sufficient and preferable. The pressure applied has a maximum set point to assure that the patient cannot apply excessive pressure during a time of distress.

In a preferred embodiment of the invention, the birth ease device includes a pair of opposed contact members each having an opposed concave surface therein forming a contact volume there between. Each opposed contact member includes a rigid concave back plate member joined at an end to a rigid connector plate member, with each back plate member having an opposed concave surface. Each opposed contact member includes a motive mechanism selectively actuated to vary the contact volume between the opposed contact members. The motive mechanism includes a plurality of inflatable bladder members secured to the opposed concave surface of each back plate member by a flexible padding member secured thereto, with each inflatable bladder member operatively connected to a pressurized fluid source. A control mechanism is operatively connected to each opposed motive mechanism to selectively increase and decrease the contact volume between the opposed contact members. The control mechanism provides selective inflation and deflation of the inflatable bladder members by the pressurized fluid source. The concave surfaces of the flexible padding members of the contact members of the birth ease device are adapted for contact with a woman's pelvis during child birth. The inflatable bladder members of the motive mechanism are selectively controlled by the woman to increase and decrease the contact volume occupied by the woman's pelvis, thereby selectively applying and releasing pressure to the woman's pelvis, and assisting delivery of a child.

BRIEF DESCRIPTION OF THE DRAWINGS

FIG. 6 is a perspective view of the birth ease device of FIG. 1 of the present invention positioned around the pelvis of a woman for assisting in child birth.

FIG. 7 is a schematic view of the motive mechanism and operatively connected control mechanism of the present invention.

DESCRIPTION OF THE EMBODIMENTS

Nomenclature

Figure 1:
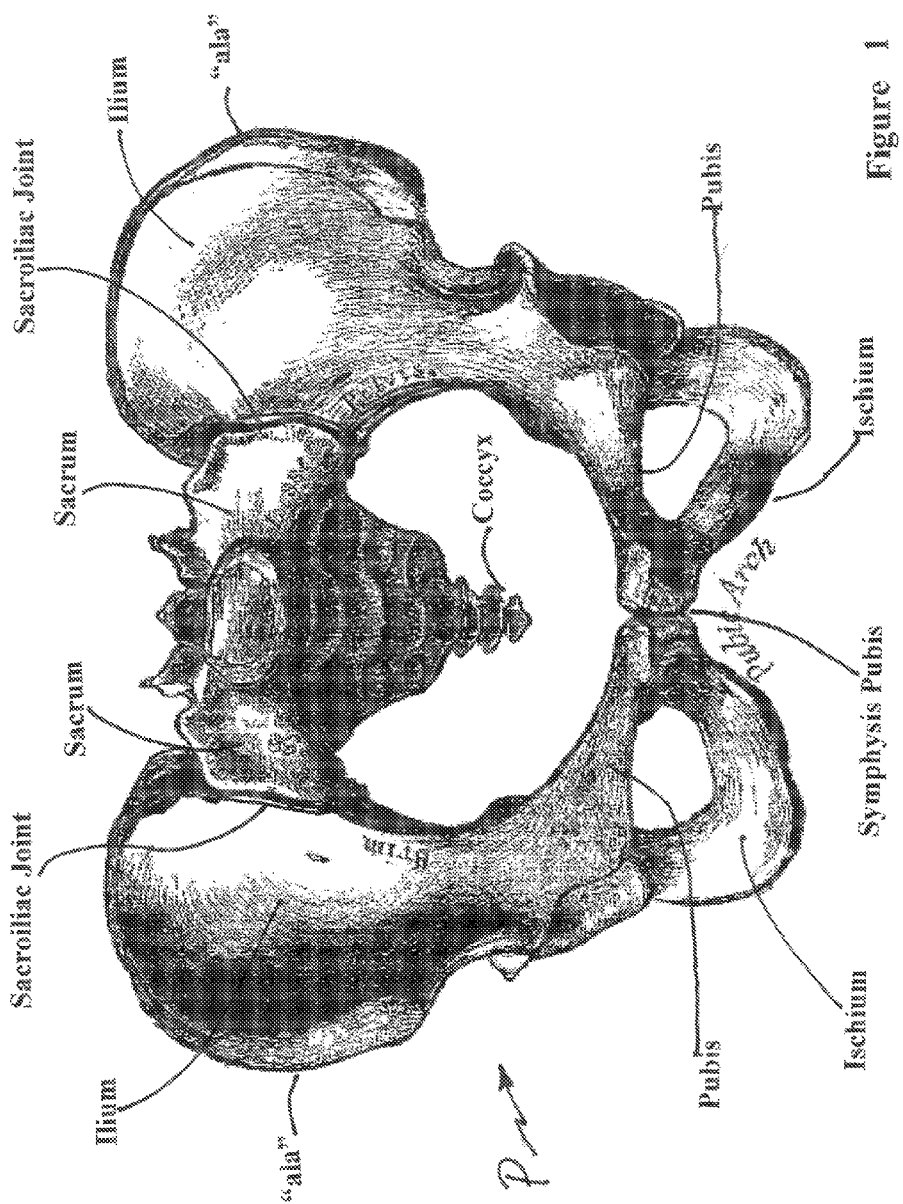
FIG. 1 is a perspective top view of the pelvis bone of a human, to which the device of the present invention is applied.

10 Birth Ease Device
20 Opposed Contact Members
22 Opposed Concave Surface of Contact Member
30 Rigid Concave Back Plate Members
32 Concave Surface of Back Plate Members
36 Rigid Ribbing of Back Plate Members
38 Aligned Apertures of Rigid Ribbing
40 Connector Plate Member
42 Hollow Cylinders
44 Fasteners for Connector Plate Members
50 Motive Mechanism
55 Inflatable Bladder Members
60 Flexible Padding Members
65 Fluid Conduit System
70 Control Valves for Bladder Members
75 Pressurized Fluid Reservoir
80 Control Mechanism
85 Master Control Valve
87 Pressure Regulators
90 Micro Controller Logic Circuit Member
95 Hand-Held Remote Control Member
98 Conductor Cord for Control Member
P Pelvis Bone
V Contact Volume Between Contact Members

CONSTRUCTION

The invention is a device for easing child birth, which is controlled by the individual giving birth to the child. The birth ease device is designed to mechanically replace a "manual" contact, which can be applied to the pelvis of a woman in labor (delivering of a baby), for the purpose of aiding the expulsion of the baby, and also significantly reducing the pain and discomfort associated with this process. The birth ease device mechanically compresses the ilium portion of the pelvis medially and posteriorly, simultaneously. The pressure applied by the birth ease device is under full control of the patient, or a qualified technician, so that the pressure is applied slowly and progressively to a point of maximum comfort, but the pressure can be decreased immediately upon demand by the patient. The duration of the application of compression corresponds with the length of the contraction period for the woman.

The birth ease device includes a pair of contact members that are contoured to fit the "ala" of the ilium and are adjustable to fit a range of sizes. The pair of opposed contact members each has an opposed concave surface therein forming a contact volume there between. Each opposed contact member includes a motive mechanism selectively actuated to vary the contact volume between the opposed contact members. A control mechanism is operatively connected to each opposed motive mechanism to selectively increase and decrease the contact volume between the opposed contact members. The motive mechanism is selectively controlled by the woman to increase and decrease the contact volume occupied by the woman's pelvis, thereby selectively applying and releasing pressure to the woman's pelvis, and assisting delivery of a child.

The birth ease device adds compressive pressure to the "ala" of the ilium. The medial pressure exerted by the birth ease device leverages the pelvis at the sacroiliac joints. This pressure is superior to a line drawn through the sacroiliac joints and causes reduced pressure inferior to this line, mainly affecting the symphysis pubis and the obturator foramen. The pressure applied by the concave, contact members eases the pressure exerted by the emerging head of the baby at the "obturator foramen." The applied pressure significantly decreases the pain associated with the birth process and aids the efficiency of the baby's head in forcing the obturator to enlarge.

For safety purposes, the pressure applied by the birth ease device is applied slowly, while reduction of the pressure must be immediate and absolute. However, a slow reduction of pressure comparable to the rate of application is sufficient and preferable. The pressure applied has a maximum set point to assure that the patient cannot apply excessive pressure during a time of distress.

In a preferred embodiment of the invention, the birth ease device includes a pair of opposed contact members each having an opposed concave surface therein forming a contact volume there between. Each opposed contact member includes a rigid concave back plate member joined at an end to a rigid connector plate member, with each back plate member having an opposed concave surface. Each opposed contact member includes a motive mechanism selectively actuated to vary the contact volume between the opposed contact members. The motive mechanism includes a plurality of inflatable bladder members secured to the opposed concave surface of each back plate member by a flexible padding member secured thereto, with each inflatable bladder member operatively connected to a pressurized fluid source. A control mechanism is operatively connected to each opposed motive mechanism to selectively increase and decrease the contact volume between the opposed contact members. The control mechanism provides selective inflation and deflation of the inflatable bladder members by the pressurized fluid source. The concave surfaces of the flexible padding members of the contact members of the birth ease device are adapted for contact with a woman's pelvis during child birth. The inflatable bladder members of the motive mechanism are selectively controlled by the woman to increase and decrease the contact volume occupied by the woman's pelvis, thereby selectively applying and releasing pressure to the woman's pelvis, and assisting delivery of a child.

Referring now to FIG. 1, a top view representation of the pelvis of a human is shown. The pelvis is a well-known anatomical structure and will not be discussed in detail. It should be noted that the approximately circular opening in the center of the pelvis is the route through which the head and body of a child passes during natural child birth.

Figure 2:
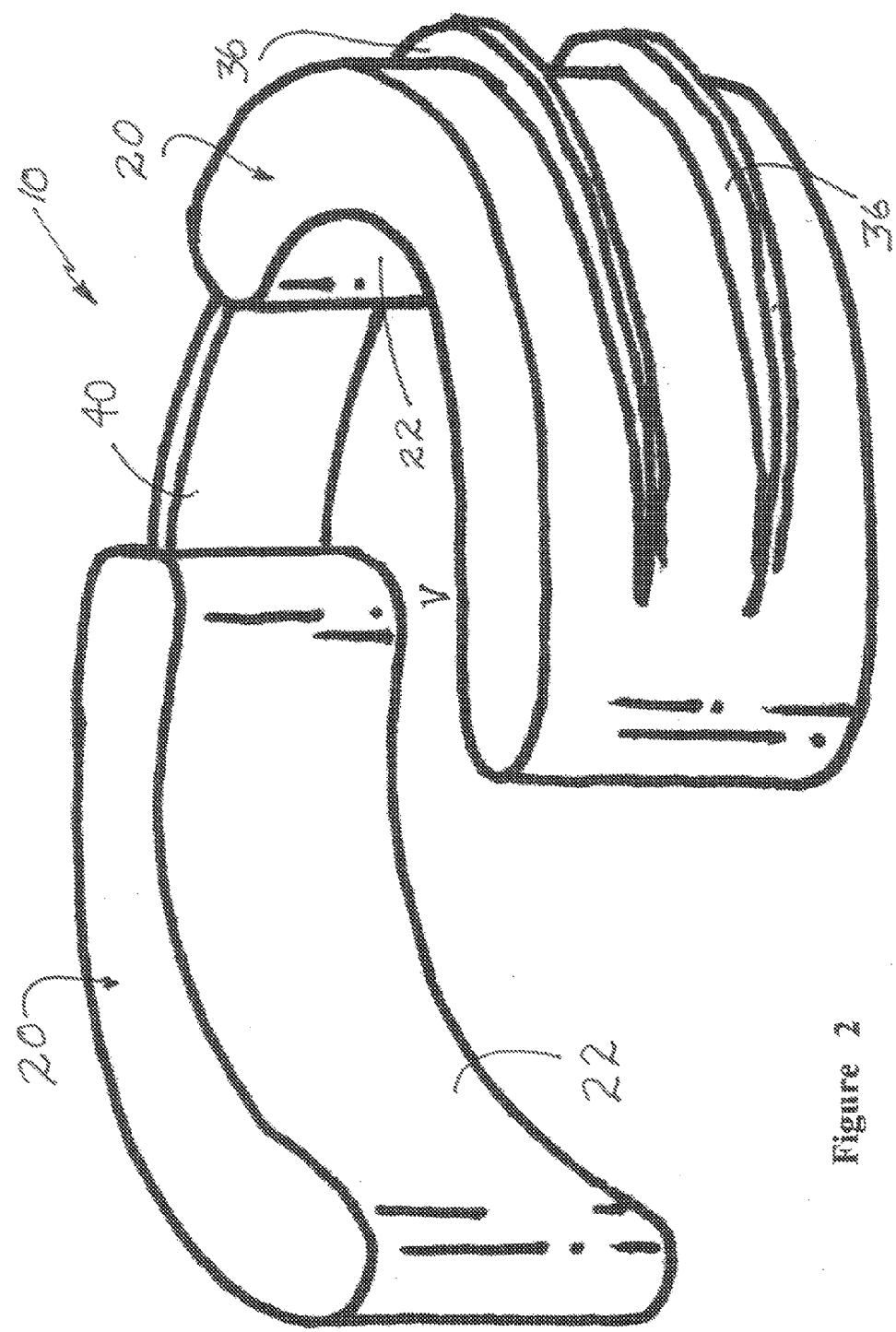
FIG. 2 is a perspective front view of one embodiment of the birth ease device of the present invention.
Figure 3:
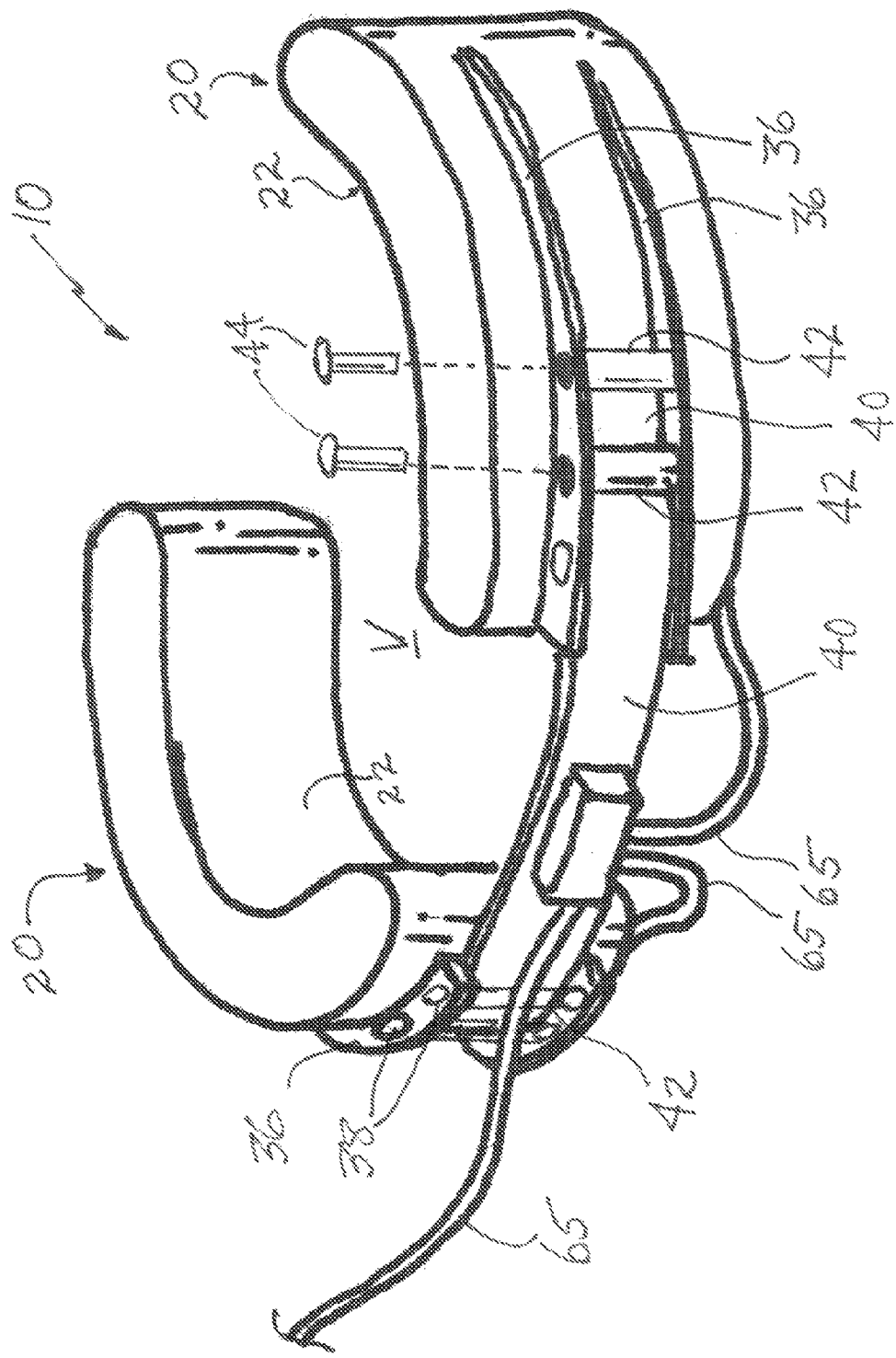
FIG. 3 is a perspective rear view of the birth ease device of FIG. 2 of the present invention.

Referring now to FIGS. 2 and 3, front and rear perspective view of one embodiment of the birth ease device 10 of the present invention are illustrated. The birth ease device 10 includes a pair of padded, concave, opposed contact members 20 that are contoured to fit the "ala" of the ilium of the expectant mother. The pair of opposed contact members 20 each has an opposed concave surface 22 therein. Each opposed contact member 20 includes a rigid concave back plate member 30 joined at an end to the other back plate member 30 via a connector plate member 40. Each concave back plate member 30 includes a pair of horizontal, rigid ribbing 36 opposite the concave surface 32 of each back plate member 30 for added strength and rigidity. The pair of rigid ribbing 36 also provides a means of securing each back plate member 30 to the connector plate member 40. For example, the connector plate member 40 is sized to fit between the pair of rigid ribbing 36 of each back plate member 30. The rigid ribbing 36 includes pairs of vertically aligned apertures 38 adjacent one end of each connector plate member 40. Each end of the connector plate member 40 includes pairs of hollow cylinders 42 spaced to align with adjacent pairs of aligned apertures 38 in the rigid ribbing 36. Fasteners 44, such as rods, pins or bolts, inserted through adjacent pairs of aligned apertures 38 and the pair of hollow cylinders 42 provide rigid connection between each back plate member 30 and the connector plate member 40. The plurality of pairs of aligned apertures 38 of the rigid ribbing 36 provide for size adjustment between the opposed contact members 20 to accommodate a wide range of individually sized expectant mothers.

Figure 4:
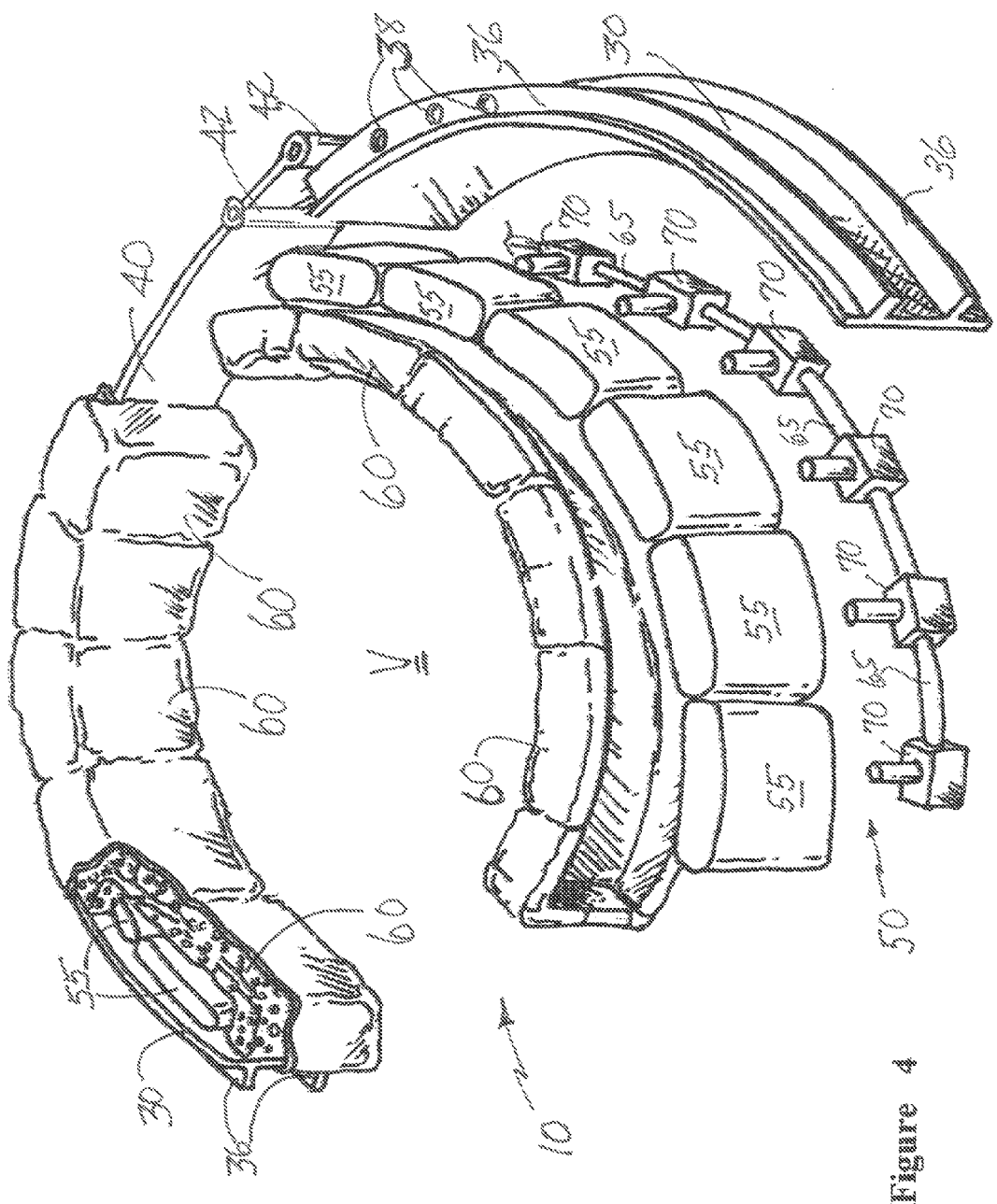
FIG. 4 is an exploded perspective front view of the embodiment of the birth ease device of FIG. 1 of the present invention.

Referring now to FIG. 4, a partially exploded, front perspective view of the birth ease device 10 is shown. A motive mechanism 50 is attached to the concave surface 32 of each opposed back plate member 30. The motive mechanism 50 is selectively actuated to cause at least one opposed contact member 20 to vary the contact volume V between the two contact members 20. The motive mechanism 50 includes a plurality of inflatable bladder members 55 secured to the opposed concave surface 32 of each back plate member 30 by a flexible padding member 60 covering the bladder members 55 and secured to each back plate member 30. Preferably, the plurality of inflatable bladder members 55 of each opposed contact member 20 are vertically aligned on each rigid concave back plate member 30, as shown in FIG. 4. Each inflatable bladder member 55 is operatively connected to a pressurized fluid source, such as a reservoir or compressor 75, via a fluid conduit system 65 with a control mechanism 80 providing selective inflation and deflation of the inflatable bladder members 55.

Details of the motive mechanism 50, pressurized fluid source 75 and control mechanism 80 are shown in FIG. 7. In this embodiment of the invention, the pressurized fluid source 75 comprises a compressor. The compressed fluid, in this embodiment air, is delivered to the bladder members 55 via the fluid conduit system 65 fitted with pressure regulators 87 and a master control valve 85. Preferably, the fluid conduit system 65 is individually connected to each bladder member 55 via a separate control valve member 70. Each control valve member 70 is individually operated by a logic circuit 90 in communication with each control valve member 70. The logic circuit 90 is operated through communications from a remote control member 95. The operation of the birth ease device 10 is achieved through a hand-held control member 95 connected to the motive mechanism 50 by a conductor cord 98. Alternatively, the hand-held control member 95 is a wireless transmitter that communicates with the control motive mechanism 50 by radio or infra-red frequencies.

Figure 5:
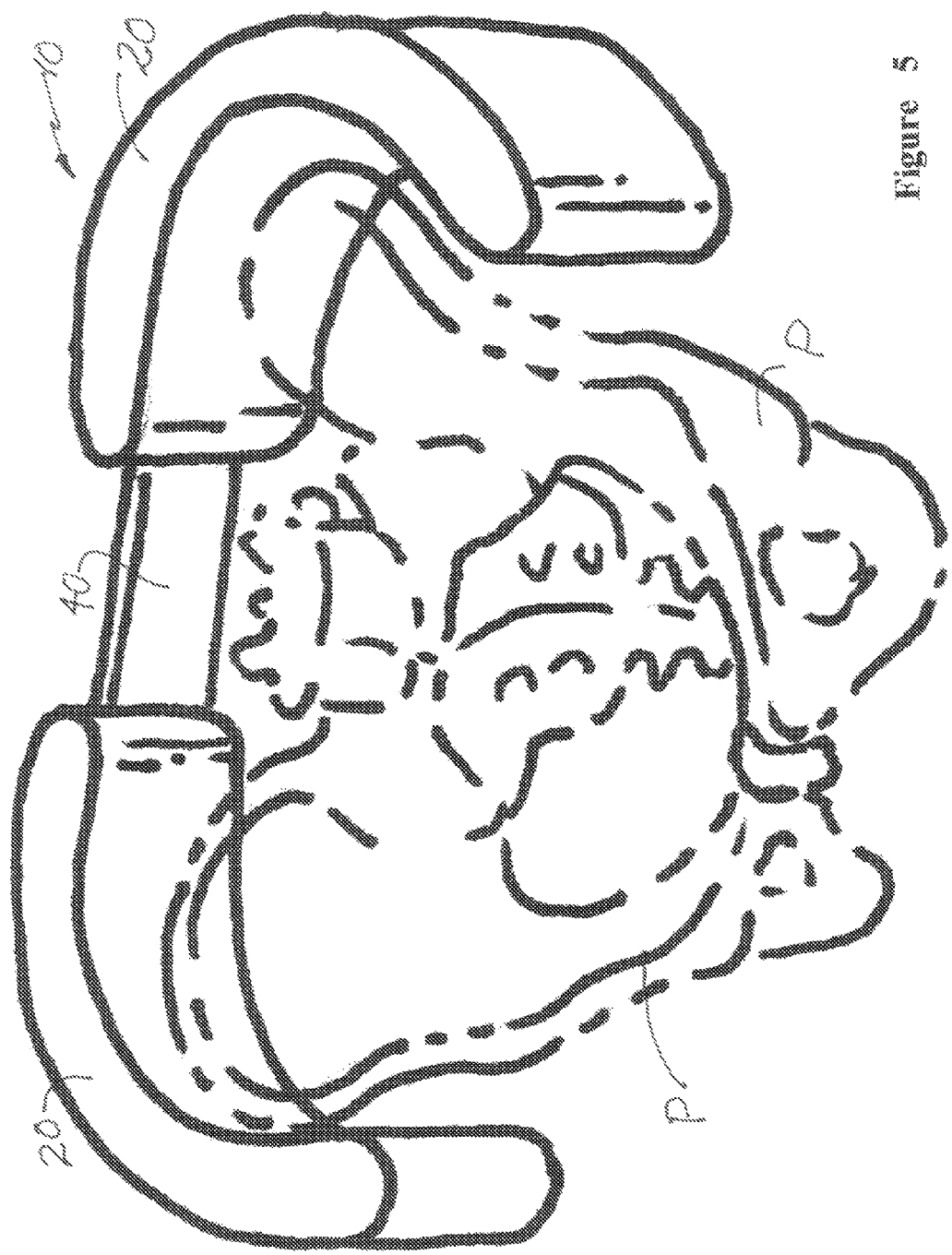
FIG. 5 is a perspective front view of the embodiment of the birth ease device of FIG. 1 of the present invention as applied to a human pelvis bone.

The birth ease device 10 is applied to the pelvis P of a woman in labor for the purpose of aiding the movement of the baby through the birth canal. As illustrated in FIGS. 5 and 6, the opposed, concave contact members 20 are positioned about the pelvis of an individual so as to contact and add compressive pressure to the "ala" of the ilium of the woman. The medial pressure exerted by the birth ease device 10 leverages the pelvis P at the sacroiliac joints. This pressure is superior to a line drawn through the sacroiliac joints and causes reduced pressure inferior to this line, mainly affecting the symphysis pubis and the obturator foramen. The pressure applied by the inflatable bladder members 55, via the flexible padding members 60, eases the pressure exerted by the emerging head of the baby at the "obturator foramen." The applied pressure significantly decreases the pain associated with the birth process and aids the efficiency of the baby's head in forcing the obturator to enlarge.

As mentioned above, the operation of the birth ease device 10 positioned about the pelvis P of an individual so as to contact and add compressive pressure to the "ala" of the ilium of the expectant mother, is controlled by that individual. Upon activated by that individual, the logic circuit 90 inflates the bladder members 55 sequentially from the open end of each opposed contact member 20 to the anchored end thereof. This sequence of inflation provides the desired compressive pressure described above. Because the operation of the birth ease device 10 is under the control of the expectant mother, direct and immediate feed back from that individual to the birth ease device 10 occurs. In addition, a safety button is provided on the remote control member 95 that immediately deflates the bladder members 55, should the expectant mother so choose.

While the invention has been particularly shown and described with reference to preferred embodiments thereof, it will be understood by those skilled in the art that various changes in form and details may be made therein without departing from the spirit and scope of the invention.

We claim:

1. A birth ease device adapted for assisting a woman in child birth, the birth ease device comprising:
a pair of opposed contact members each having an opposed concave surface therein forming a contact volume there between, each opposed contact member including a rigid back plate member rigidly joined at an end to a connector plate member, each back plate member having an opposed concave surface, each opposed contact member including a motive mechanism selectively actuated to vary the contact volume between the opposed contact members, the motive mechanism including a plurality of inflatable bladder members, each opposed concave surface of each backplate member having a plurality of individual inflatable bladder members secured to the opposed concave surface of each back plate member by a corresponding plurality of flexible padding members; and
a control mechanism operatively connected to each opposed motive mechanism to selectively increase and decrease the contact volume between the opposed contact members;
whereby the concave surfaces of the contact members of the birth ease device are adapted for contact with a woman's pelvis during child birth, the motive mechanism selectively controlled by the woman to increase and decrease the contact volume occupied by the woman's pelvis, thereby selectively applying and releasing pressure to the woman's pelvis, and assisting delivery of a child.

2. The birth ease device adapted for assisting a woman in child birth of claim 1, wherein the plurality of inflatable bladder members of each opposed contact member are vertically aligned on each rigid concave back plate member.

3. The birth ease device adapted for assisting a woman in child birth of claim 1, wherein each inflatable bladder member is operatively connected to a pressurized fluid source with the control mechanism providing selective inflation and deflation of the inflatable bladder members.

4. The birth ease device adapted for assisting a woman in child birth of claim 3, wherein each inflatable bladder member is operatively connected to the pressurized fluid source by a conduit system, and operation of each inflatable bladder member individually controlled by the control mechanism via an associated valve member in the conduit system.

5. The birth ease device adapted for assisting a woman in child birth of claim 4, wherein the control mechanism includes a master valve member regulating pressurized fluid to the conduit system, and a logic circuit for selective inflation and deflation of the plurality of inflatable bladder members.

6. The birth ease device adapted for assisting a woman in child birth of claim 5, further including a remote control member operatively connected to the logic circuit providing selective inflation and deflation of the plurality of inflatable bladder members.

7. A birth ease device adapted for assisting a woman in child birth, the birth ease device comprising:
- a pair of opposed contact members each having an opposed concave surface therein forming a contact volume there between, each opposed contact member including a rigid concave back plate member rigidly joined at an end to a connector plate member, each back plate member having an opposed concave surface;
- each opposed contact member including a motive mechanism selectively actuated to vary the contact volume between the opposed contact members, the motive mechanism including a plurality of vertically aligned inflatable bladder members secured to each opposed concave surface of each back plate member by a corresponding plurality of flexible padding member, each vertically aligned inflatable bladder member on each rigid concave back plat member operatively connected to a pressurized fluid source; and
- a control mechanism operatively connected to each opposed motive mechanism to selectively increase and decrease the contact volume between the opposed contact members, the control mechanism providing selective inflation and deflation of the vertically aligned inflatable bladder members by the pressurized fluid source;
- whereby the concave surfaces of the flexible padding members of the contact members of the birth case device arc adapted for contact with a woman's pelvis during child birth, the vertically aligned inflatable bladder members of the motive mechanism are selectively controlled by the woman to increase and decrease the contact volume occupied by the woman's pelvis, thereby selectively applying and releasing pressure to the woman's pelvis, and assisting delivery of a child.

8. The birth ease device adapted for assisting a woman in child birth of claim 7, wherein each inflatable bladder member is operatively connected to the pressurized fluid source by a conduit system, and operation of each inflatable bladder member individually controlled by the control mechanism via an associated valve member in the conduit system.

9. The birth ease device adapted for assisting a woman in child birth of claim 8, wherein the control mechanism includes a master valve member regulating pressurized fluid to the conduit system, and a logic circuit for selective inflation and deflation of each of the plurality of inflatable bladder members.

10. The birth ease device adapted for assisting a woman in child birth of claim 9, further including a remote control member operatively connected to the logic circuit providing selective inflation and deflation of the plurality of inflatable bladder members.

* * * * *